(12) United States Patent
Feiweier et al.

(10) Patent No.: US 10,989,781 B2
(45) Date of Patent: Apr. 27, 2021

(54) MAGNETIC FIELD MAP DETERMINATION IN A MAGNETIC RESONANCE SYSTEM

(71) Applicant: Siemens Healthcare GmbH, Erlangen (DE)

(72) Inventors: Thorsten Feiweier, Poxdorf (DE); Daniel Niederlöhner, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 338 days.

(21) Appl. No.: 16/106,284

(22) Filed: Aug. 21, 2018

(65) Prior Publication Data
US 2019/0064302 A1 Feb. 28, 2019

(30) Foreign Application Priority Data
Aug. 28, 2017 (EP) .................... 17188159

(51) Int. Cl.
*G01R 33/565* (2006.01)
*G01R 33/48* (2006.01)
(Continued)

(52) U.S. Cl.
CPC ........ *G01R 33/56563* (2013.01); *A61B 5/055* (2013.01); *G01R 33/243* (2013.01);
(Continued)

(58) Field of Classification Search
None
See application file for complete search history.

(56) References Cited

U.S. PATENT DOCUMENTS

| 5,614,827 A | 3/1997 | Heid |
| 8,362,771 B2 | 1/2013 | Dornhaus et al. |

(Continued)

FOREIGN PATENT DOCUMENTS

EP 3336567 A1 6/2018

OTHER PUBLICATIONS

European Search Report for corresponding Application No. 17188159.2-1022, dated Mar. 22, 2018.

*Primary Examiner* — Douglas X Rodriguez
(74) *Attorney, Agent, or Firm* — Lempia Summerfield Katz LLC (57) ABSTRACT

A method and system for determining a magnetic field map in a MR system based on position of a movable patient support of the MR system are provided, wherein a first resulting field map including position dependent information about a magnetic field distribution in a homogeneity volume including an examination volume of the MR system is provided when the movable patient support is located at a first position, wherein a stationary field map including information about a magnetic field distribution in the homogeneity volume is provided, which is independent of the position of the movable patient support, wherein a position dependent field map including information about a magnetic field distribution in the homogeneity volume mainly influenced by a position of the movable patient support is determined using the stationary field map and the first resulting field map, and wherein a second resulting field map in the homogeneity volume is determined when the movable patient support is located at a second position different from the first position, using the stationary field map and the position dependent field map.

19 Claims, 4 Drawing Sheets

(51) Int. Cl.
*G01R 33/54* (2006.01)
*G01R 33/24* (2006.01)
*A61B 5/055* (2006.01)
*G01R 33/44* (2006.01)
*G01R 33/30* (2006.01)
*G01R 33/561* (2006.01)
*G01R 33/56* (2006.01)

(52) U.S. Cl.
CPC ......... *G01R 33/307* (2013.01); *G01R 33/443* (2013.01); *G01R 33/4828* (2013.01); *G01R 33/543* (2013.01); *G01R 33/246* (2013.01); *G01R 33/565* (2013.01); *G01R 33/5608* (2013.01); *G01R 33/5615* (2013.01); *G06T 2207/10088* (2013.01); *G06T 2207/30004* (2013.01)

(56) References Cited

U.S. PATENT DOCUMENTS

| | | | |
|---|---|---|---|
| 9,244,144 B2 * | 1/2016 | Blumhagen | G01R 33/56563 |
| 2008/0015431 A1 | 1/2008 | Schmitt | |
| 2010/0182007 A1 * | 7/2010 | Dornhaus | G01R 33/56375 324/309 |
| 2010/0289492 A1 | 11/2010 | Biber et al. | |
| 2015/0015257 A1 | 1/2015 | Fautz | |
| 2015/0077115 A1 | 3/2015 | Fautz et al. | |
| 2015/0204955 A1 | 7/2015 | Gumbrecht et al. | |

\* cited by examiner

MAGNETIC FIELD MAP DETERMINATION IN A MAGNETIC RESONANCE SYSTEM

The application claims the benefit of European Patent Application No. EP 17188159.2, filed Aug. 28, 2017, which is hereby incorporated by reference in its entirety.

TECHNICAL FIELD

The present disclosure relates to a method for determining a magnetic field map in a magnetic resonance (MR) system, and in particular to a method for determining a magnetic field map in a MR system based on position of a movable patient support of the MR system. Further, a corresponding MR system, computer program product, and electronically readable data carrier are provided.

BACKGROUND

Magnetic Resonance Imaging (MRI) is based on spins of atomic nuclei aligned in a magnetic B0 field. For many applications, homogeneity of the magnetic B0 field, which means constant field intensity in a large three-dimensional space, the so-called homogeneity volume of the MR system, is crucial for MR image quality and for spatial registration of MR images in regard of MR image distortions.

Common superconducting magnets allow magnetic field homogeneities with deviations of less than 1 ppm over a homogeneity volume of about 30-40 cm spherical diameter within a MR system. Accordingly, problems with fat saturation arise in regions of the anatomy located in the periphery of the above homogeneity volume, such as a shoulder of an examination subject, which cannot be disposed in the center of the homogeneity volume because of the lack of space in the patient tunnel of an MR system.

The body of an examination subject generates additional magnetic field inhomogeneities when introduced into the magnetic B0 field. The human tissue has a relative magnetic permeability different from air. As a result, the discontinuities of air and tissue lead to strong B0 distortions. Also, the inhomogeneous distribution of water, air, bone, and fat in the human body leads to a different distortion of the magnetic B0 field for each examination subject.

In order to suppress B0 inhomogeneity caused by the tissue, shim coils, which may be part of a gradient coil, or local shim coils, which may be extra coils or part of local coils, so-called CoilShim, are commonly used. In order to obtain optimal results, the current through the shim coils is optimized so that the B0 field becomes as homogeneous as possible in the homogeneity volume.

Different distortions of the magnetic fields may be taken into account. First, there are stationary known distortions, such as the fundamental magnetic field of the magnet of the MR system, the non-ideal fields of gradient coils and stationary shim coils, and all further magnetic field inhomogeneities, which are stationary and known in the so-called device coordinate system (DCS). As a different example, distortions of the magnetic field may occur when the examination subject or other objects are moved together with a movable patient support of the MR system.

Accordingly, a description of the magnetic fields may be provided as follows:

$$B(x, y, z, SHIM, TP) = B^{hom} + B'_{DCS}(SHIM^{stat}) + B_{table}(TP, SHIM^{move})$$
$$= B_{DCS}(SHIM^{stat}) + B_{table}(TP, SHIM^{move})$$

Therein, $B(x,y,z,SHIM,TP)$ corresponds to the actual distribution of the magnetic field in the patient tunnel with all contributions from the scanner and the examination subject. This actual distribution is determined by a field map measurement and it is dependent on overall shim condition $SHIM^{stat}=SHIM^{move}$) including a contribution $SHIM^{stat}$, which in one embodiment is generated by three stationary gradient shim coils, and a contribution $SHIM^{move}$, which in one embodiment is generated by five $2^{nd}$ order shim coil channels (e.g., Coilshims) and in another embodiment is generated by two $2^{nd}$ order shim coil channels (e.g., Coilshims), which are moved together with the patient support, and table position TP. Further, the magnetic field $B^{hom}$ corresponds to an ideal homogeneous magnetic field, which is not further considered here and, therefore, is integrated into the magnetic field $B_{DCS}(SHIM^{stat})$. Magnetic field $B'_{DCS}(SHIM^{stat})$ contains all inhomogeneities stationary in the DCS, e.g., which do not change when a movable patient support is moved. These are, for the most part, already known or may be determined by calibration measurements. This is also dependent on the shim state SHIM, e.g., the shim currents. The magnetic field $B_{DCS}(SHIM^{stat})$ contains the homogeneous magnetic field $B^{hom}$ for simplification. Magnetic field $B_{table}(TP,SHIM^{move})$ contains all inhomogeneities that move along with a movement of a movable patient support of the MR system, in particular, a movement of the patient support with the examination subject in the DCS. These inhomogeneities are dominated by the susceptibility distribution of the examination subject and therefore are largely undetermined. $B_{table}(TP, SHIM^{move})$ is known in the table coordinate system, in particular, when the position of the Coilshims and the current through the Coilshims are known, apart from patient movement and other arbitrary distortions. In particular, $B_{table}(TP,SHIM^{move})$ moves in the same extent as the table in the DCS and is, therefore, directly dependent on the table position TP in the MR system.

With common MR imaging methods for determining a magnetic field map in a MR system, these two magnetic field components $B_{DCS}$ and $B_{table}$ are not any further separable and thus the following disadvantages arise according to these known MR imaging methods.

As a first disadvantage, the field map, (on which shimming is based), is measured newly after movement of the table, with a small tolerance threshold.

Further, field maps based on so-called Move-During-Scan (MDS) adjustments are isocentrically determined, and accordingly only have a few centimeters of coverage in z-direction of the table and may therefore only be used isocentrically.

Commonly, the magnetic field at a certain table position are determined by a 2-echo field map measurement, as described in U.S. Pat. No. 5,614,827 A, for example. Therein, a phase difference between a first and second echo is used as measure of the magnetic field homogeneity and the phase difference is further spatially differentiated by a respective difference to each neighbor in each of the three spatial directions, due to occurring phase wraps, in order to determine shim settings.

These data are commonly used in combination with likewise spatially differentiated coil fields to calculate shim currents. In particular, due to the occurring phase wraps and the subsequent spatial differentiation, no direct determination of the magnetic field is possible.

In the 2-echo field map measured as described above, the inhomogeneities $B_{table}$, which are caused by distortions of the magnetic field by the examination subject and the patient support, are superposed with inhomogeneities of the basic magnetic field B0 and further components $B_{DCS}$. These two components of the magnetic field are not uniquely separable in the 2-echo method due to the occurring phase wraps.

If the table position changes, then the field map is remeasured, because in the DCS the following applies:

$$B_{table}(TP1,SHIM^{move}) \neq B_{table}(TP2,SHIM^{move})$$

For very small table movements, it may be assumed that $B_{table}(TP1,SHIM^{move})$ and $B_{table}(TP2,SHIM^{move})$ do not differ much, and thus a limit value for $\Delta TP$ is defined, so that the field map is not measured anew for reasons of time savings in the case of very small table movements.

In the case of the MDS adjustments, only the gradients and not the 2nd order shims are used because of the above restrictions. Furthermore, the shim setting is calculated based on the information of a field map extending only a few centimeters in the z-direction but is used for larger volumes. This results in a corresponding loss of quality.

Methods to determine a field map are known from U.S. Patent Application Publication No. 2015/0015257 A1 and U.S. Patent Application Publication No. 2015/0077115 A1.

SUMMARY

Accordingly, there is a need to provide a method for a MR system with a movable patient support, which provides a high-quality and more efficient determination of a magnetic field map compared to known methods and systems.

The scope of the present disclosure is defined solely by the appended claims and is not affected to any degree by the statements within this description. The present embodiments may obviate one or more of the drawbacks or limitations in the related art.

According to a first aspect, a method for determining a field map in a MR system including a movable patient support is provided. Therein, in one act, a first resulting field map including position dependent information about a magnetic field distribution in a homogeneity volume including an examination volume of the MR system is provided when the movable patient support is located at a first position. In a further act, a stationary field map including information about a magnetic field distribution in the homogeneity volume is provided, which is independent of the position of the movable patient support. In another act, a position dependent field map including information about a magnetic field distribution in the homogeneity volume mainly influenced by a position of the movable patient support is determined using the stationary field map and the first resulting field map. In a further act, a second resulting field map in the homogeneity volume is determined when the movable patient support is located at a second position different from the first position, using the stationary field map and the position dependent field map.

Thereby, an improved method for determining a magnetic field map in a MR system is provided, according to which an absolute B0 field map is used and magnetic field inhomogeneities are first separated into stationary magnetic field components and patient support position dependent magnetic field components, in order to then add these components again to determine a magnetic field map based on a new desired table position based on a calculation and not a measurement, as commonly carried out. Further, previous measurements of the magnetic field map based on certain table positions may be saved and reused, even if the table is moved more than a specified table movement threshold, which commonly initiates a new magnetic field map measurement. Effectively, a significantly larger value for the patient support movement threshold may be used, e.g., the patient support may be moved to a greater extend before a new measurement of the magnetic field map has to be initiated. This results in saving of adjustment time and thus gives the customer more time for imaging protocols—without any qualitative degradation. Especially in the case of the scan-at-center concept, a larger value for the table movement threshold may be particularly helpful measuring time may be saved significantly. Furthermore, the determined magnetic field map may be used for the calculation of high-quality shim settings, so that an efficient and precise homogenization of the magnetic B0 field is provided.

According to a second aspect, a method for determining a change of a stationary magnetic field in a MR system with a movable patient support is disclosed. Therein, in an act, a resulting field map is provided for each of a plurality of different positions of the movable patient support, wherein the resulting field map is based on a stationary magnetic field substantially not influenced by position of the movable patient support and a position dependent magnetic field mainly influenced by each position of the movable patient support. In a further act, the plurality of resulting field maps is averaged, e.g., an average is calculated between a plurality of resulting magnetic field values for each voxel. In another act, a change of the stationary magnetic field of the MR system is determined based on the average of the plurality of resulting field maps.

Thereby, an improved method for determining a change of a stationary magnetic field in a MR system is provided, according to which an absolute B0 field map is used and magnetic field inhomogeneities are separated into stationary magnetic field components and table position dependent magnetic field components, in order to determine a change of the stationary magnetic field of the MR system. The influences of non-stationary magnetic fields are averaged, leaving a measure for the actual scanner inhomogeneity and thus stationary contributions of the basic magnetic field due to external influences, e.g. installation of another large device in the immediate neighborhood, may be reliably detected.

The MR system for determining a magnetic field map described in the second aspect may be configured to perform any of the methods described in the first aspect described above. For such systems for determining a magnetic field map, technical effects may be achieved, which correspond to the technical effects described for the method for determining a magnetic field map according to the first aspect.

According to a third aspect, a MR system for determining a magnetic field map is provided, wherein the system includes the following elements. The MR system includes a memory configured to store program code, and least one MR controller coupled with the memory. Therein, the at least one MR controller is configured to execute the program code, wherein execution of the program code causes the MR system to perform the following acts. In one act, a first resulting field map including position dependent information about a magnetic field distribution in a homogeneity volume including an examination volume of the MR system is provided when the movable patient support is located at a first position. In a further act, a stationary field map including information about a magnetic field distribution in the homogeneity volume is provided, which is independent of the position of the movable patient support. In another act, a position dependent field map including information about a magnetic field distribution in the homogeneity volume mainly influenced by a position of the movable patient support is determined using the stationary field map and the first resulting field map. In a further act, a second resulting field map in the homogeneity volume is determined when the movable patient support is located at a second position different from the first position, using the stationary field map and the position dependent field map.

According to a fourth aspect, a computer program product is provided, which includes program code, which may be loaded directly into a memory of a MR system, wherein execution of the program code by a MR controller causes the MR system to perform one of the methods as described in the first aspect above.

According to a fifth aspect, an electronically readable data carrier is provided with electronically readable control information stored thereon, which are configured in such a way that they execute one of the methods as described in the first aspect above when using the data carrier in a MR controller of a MR system.

Although specific features described in the above summary and the following detailed description are described in connection with specific embodiments and aspects of the present disclosure, it should be understood that the features of the exemplary embodiments and aspects may be combined with each other unless specifically noted otherwise.

BRIEF DESCRIPTION OF THE DRAWINGS

The present disclosure will now be described in more detail with reference to the accompanying drawings.

DETAILED DESCRIPTION

In the following, concepts in accordance with exemplary embodiments will be explained in more detail and with reference to the accompanying drawings.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, modules, or other physical or functional units shown in the drawings or described herein may also be implemented by a direct or indirect connection or coupling. A coupling between components may also be established over a wireless connection. Functional blocks may be implemented in hardware, firmware, software, or a combination thereof.

Figure 1:
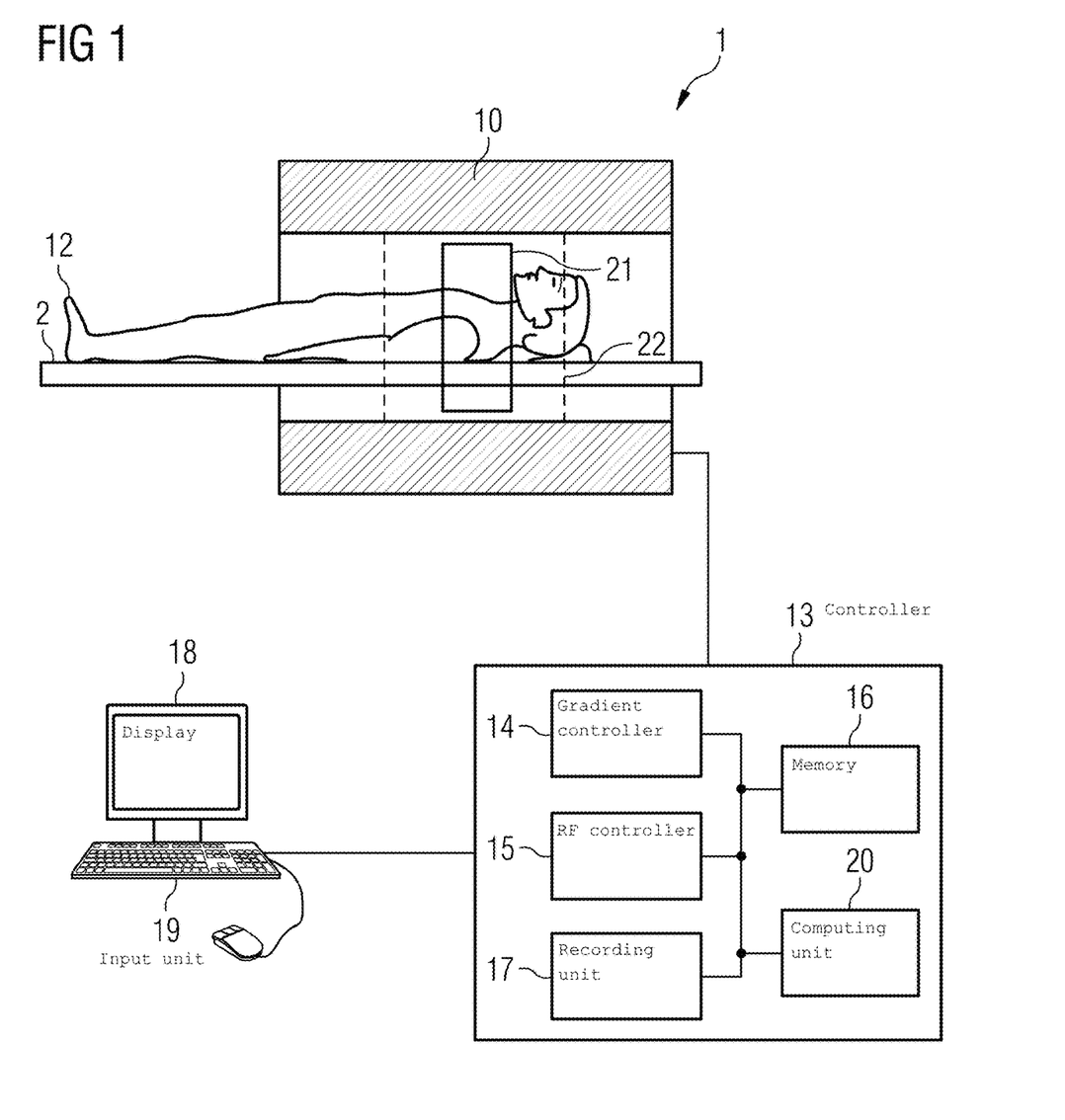
FIG. 1 illustrates a schematic drawing of a MR system including a movable patient support with which a method for determining a field map may be carried out, according to certain embodiments.

FIG. 1 illustrates a schematic drawing of an MR system 1 including a movable patient support 2 with which a method for determining a field map may be carried out, according to certain embodiments.

Referring to FIG. 1, an MR system 1 is described, with which, as explained below, a magnetic field map may be determined based on position of a patient support. An examination subject 12, or an examining object, is located in an examining tunnel of MR system 1. The MR system 1 includes a magnet 10 for generating a basic field B0, whereby an examination subject 12 is positioned on a patient support 2, (e.g., patient table), of the MR-system. Inside the magnet, a homogeneity volume 22 including an examination volume 21 is formed. The patient support 2 is moved in the center of the magnet 10 into the homogeneity volume 22 including an examination volume 21, such that the MR system receives spatially coded magnetic resonance signals from the examination volume 21. By irradiation of RF pulse sequences and switching of magnetic field gradients, the nuclear spins in the examination volume 21 may be deflected from the equilibrium position and currents induced by the magnetization generated by the base field B0 and the return to the equilibrium position may be converted into magnetic resonance signals in the receiving coils. The general mode of operation for the generation of MR images and the detection of the magnetic resonance signals are known to a person skilled in the art, so that a detailed explanation thereof is omitted in the following.

The MR system 1 includes a MR controller 13, which is used for controlling the MR system 1. The central MR controller 13, which is configured to perform the method described below for determining a field map, further includes a gradient controller 14 for controlling and switching the magnetic field gradients, and a RF controller 15 for controlling and irradiating the RF pulses for deflecting the nuclear spins from the equilibrium position. In a memory unit 16, for example, the imaging sequences necessary for recording the MR images may be stored, as well as the programs which are necessary for the operation of the MR system 1. A recording unit 17 controls the image recording and thus controls the sequence of the magnetic field gradients and RF pulses and the reception intervals of MR signals as a function of the selected imaging sequences. The recording unit 17 also controls the gradient control 14 and the HF control 15. MR images, which may be displayed on a display 18, may be calculated in a computing unit 20, whereby an operator operates the MR system via an input unit 19. The memory 16 may have imaging sequences and program modules which carry out the method when executed in the computing unit 20 of one of the modules shown. The RF controller 15 may further be configured to improve the method for determining a magnetic field map, as is explained in the following in detail. In particular, memory 16 stores control information which may be derived from the MR controller 13. Further, the recording unit 17 is configured to perform the following method for determining a magnetic field map.

The MR system of FIG. 1 is configured in such a way that, during the execution of the control information in the MR controller 13, a method for determining a field map is performed.

Figure 2:
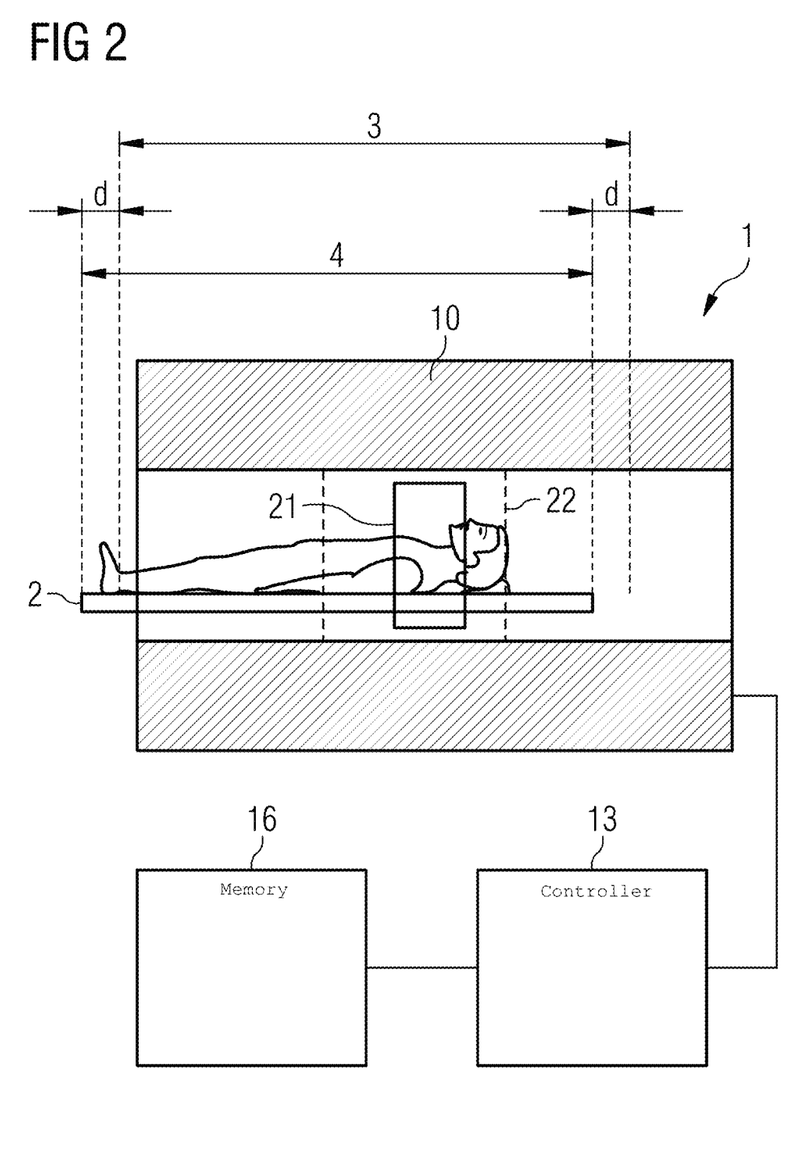
FIG. 2 illustrates a schematic drawing of another MR system including a movable patient support in a first and second position, according to certain embodiments.

FIG. 2 illustrates a schematic drawing of another MR system 1 including a movable patient support 2 in a first position 3 and a second position 4.

The MR system 1 illustrated in FIG. 2 is designed similar to MR system 1 illustrated in FIG. 1, wherein MR system 1 includes a movable patient support 2, a magnet 10, a homogeneity volume 22, an examination volume 21, a memory 16 configured to store program code, and an MR controller 13 coupled with the memory 16 and configured to execute the program code. The patient support 2 may be located at different positions within MR system 1. For example, the patient support 2 may be located at a first position 3 within MR system 1, as shown in FIG. 2, or patient support 2 may be located at a second position 4 within MR system 1 differing from the first position 3 by a displacement d.

The basic idea is the separation of $B_{DCS}(SHIM)$ and $B_{table}(TP)$. This is made possible by use of a so-called absolute field map, which may for example be based on the 3-echo method, as described, for example, in U.S. Patent Application Publication No. 2015/0204955 A1, or other methods as known in the art. A further prerequisite is the knowledge of $B_{DCS}(SHIM)$.

This is the case because the significant contributions are known: The basic magnetic field is measured during installation of the MR system and the non-ideal components of the gradients and shims are also known. Thus, the table-fixed inhomogeneities may be calculated from the measured absolute field map and handled separately:

$$B_{table}(x,y,z,TP1,SHIM^{move}) = B(x,y,z,SHIM,TP1) - B_{DCS}(x,y,z,SHIM^{stat})$$

These two components $B_{table}(TP1,SHIM^{move})$ and $B_{DCS}(SHIM^{stat})$ are stored separately and used for further calculation of a field map at a different table position:

$$B(x,y,z,SHIM,TP2) = B_{DCS}(x,y,z,SHIM^{stat}) + B_{table}(x,y,z,SHIM^{move},TP1,TP2)$$

Assuming that the table only moves along the z-coordinate, the following relation applies to table positions TP1 at $z_{TP1}$ and TP2 at $z_{TP2}$:

$$B(x,y,z,SHIM,TP2) = B_{DCS}(x,y,z,SHIM^{stat}) + B_{table}(x,y,z-z_{TP1}+z_{TP2},SHIM^{move},TP1)$$

The spatial extent of the magnetic field $B_{table}$ (TP) is limited to the spatial extent of the measured field map and thus to the homogeneity volume. A calculation of the field map over the total homogeneity volume is not possible. However, if the next diagnostic measurement at table position TP2 requires information about a region with limited extent along the z-direction only, then the information measured before may still be sufficient.

As an example, in a first measurement, a field map is determined over a range in z-direction extending over 30 cm, e.g., the magnetic field is known over +/−15 cm. In a second measurement at table position TP2=TP1+10 cm, the field map may be determined in a range from −5 cm to +25 cm. For example, if the second measurement only covers a centered stack of layers with an extension of 10 cm, then no new field map may have to be measured.

For strongly varying table positions, there is not enough information to calculate B(x,y,z,SHIM,TP2). A new measurement is therefore necessary in this case. If TP1 and TP2 do not differ by more than the extension of the field map measurement in z-direction minus a tolerance value, then $B_{table}(TP1,SHIM^{move})$ and $B_{table}(TP2,SHIM^{move})$ complement each other to a correspondingly larger information, which is longer in z-direction. Then, a field map B(x,y,z,SHIM,TP3) may also be calculated directly at a table position TP3 between TP1 and TP2.

Figure 3:
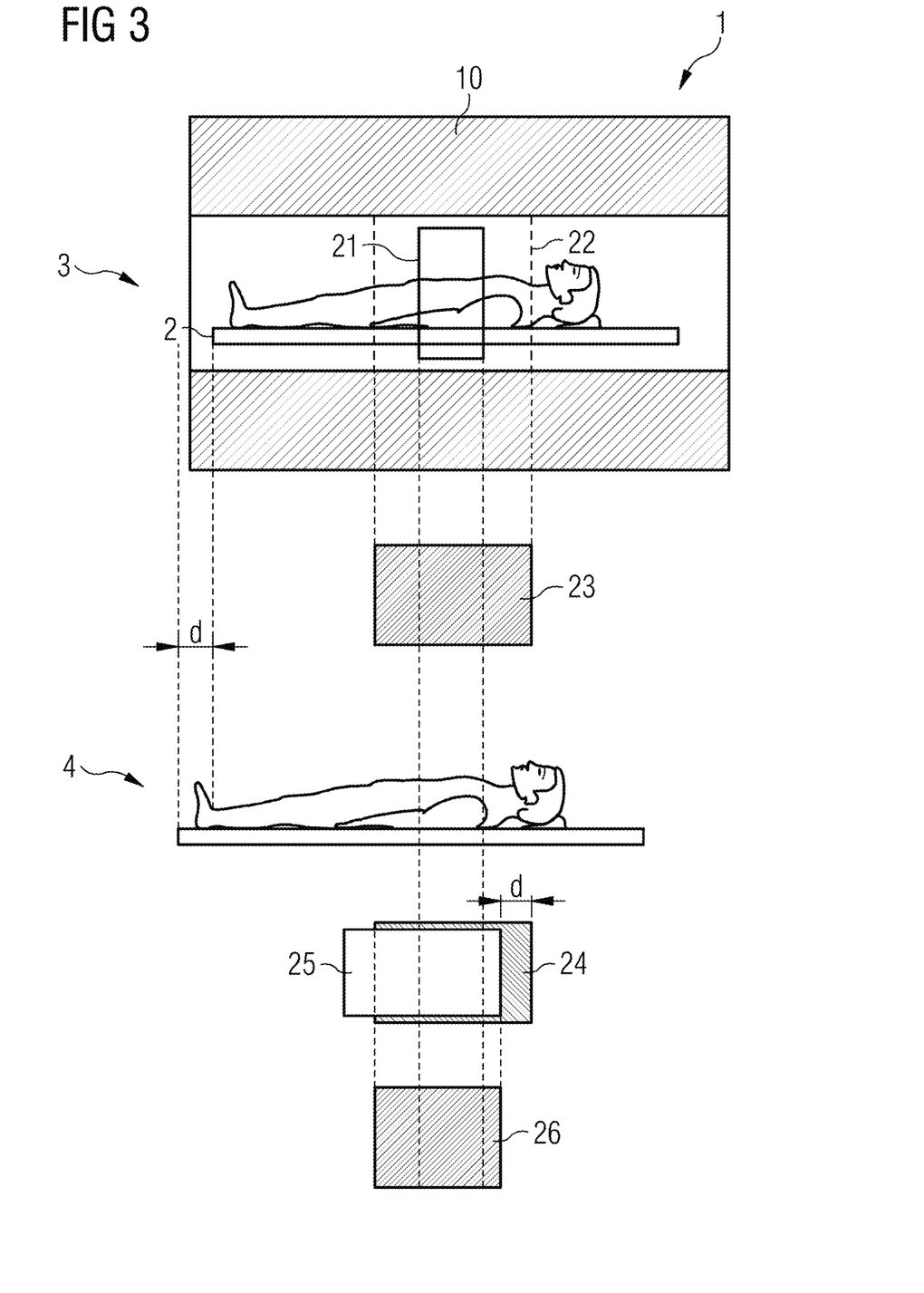
FIG. 3 illustrates a schematic drawing of the MR system of FIG. 2 with corresponding magnetic field maps, according to certain embodiments.

FIG. 3 illustrates a schematic drawing of the MR system 1 of FIG. 2 with corresponding magnetic field maps.

A first resulting field map 23 corresponds to a first position of the patient support 2 in MR system 1. After displacing the patient support 2 by displacement d, the patient support is disposed at a second position 4. Along with the patient support 2, the position dependent magnetic field map, which may be only dependent of elements moved together with the patient support 2, is also displaced by displacement d. The MR system 1, as illustrated in FIGS. 2 and 3, may therefore determine a second magnetic field, when the movable patient support 2 is located at a second position 4 different from the first position 3, using the stationary field map 24 and the position dependent field map 25. In particular, execution of the program code by the MR controller 13 may cause the MR system 1 to perform the method according to the following acts. In one act, a first resulting field map 23 including position dependent information about a magnetic field distribution in homogeneity volume 22 including examination volume 21 of the MR system 1 is provided when the movable patient support 2 with examination subject 12 is located at a first position 3. In a further act, a stationary field map 24 including information about a magnetic field distribution in homogeneity volume 22 is provided, which is independent of the position of the movable patient support 2. In particular, the stationary field map includes magnetic field components of the stationary shim coils, and therefore, even when the currents through the stationary field coils change, the changed stationary field map may be calculated using the changed currents through the stationary shim coils. Likewise, the position dependent field map 25 includes magnetic field components of the movable shim coils, (e.g., Coilshims), wherein when the currents through the movable shim coils change, the changed position dependent field map may be calculated using the changed currents through the movable shim coils. In another act, a position dependent field map 25 including information about a magnetic field distribution in homogeneity volume 22 mainly influenced by a position of the movable patient support 2 is determined using the stationary field map 24 and the first resulting field map 23. In a further act, a second resulting field map 26 in the homogeneity volume 22 is determined when the movable patient support 2 is located at a second position 4 different from the first position 3, using the stationary field map 24 and the position dependent field map 25. In one embodiment, the second resulting field map is determined in a volume, which is smaller than the homogeneity volume 22, e.g., as small as the intersection of stationary field map 24 and position dependent field map 25. In another embodiment, the above-described method may be performed for an arbitrary volume within MR system 1 other than the homogeneity volume 22, e.g., a second resulting field map may be determined for an arbitrary other volume than homogeneity volume, e.g., only the examination volume 21.

Figure 4:
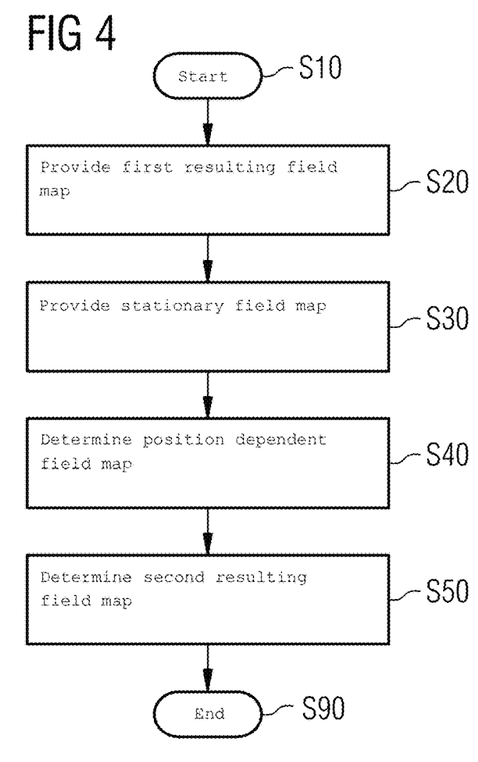
FIG. 4 schematically illustrates a flow chart with acts for performing a method for determining a field map in an MR system with a movable patient support, according to certain embodiments.

FIG. 4 schematically illustrates a flow chart with acts for performing a method for determining a field map in an MR system 1 with a movable patient support 2.

The method starts in act S10. In act S20, a first resulting field map 23 including position dependent information about a magnetic field distribution in a homogeneity volume 22 including an examination volume 21 of the MR system 1 is provided when the movable patient support 2 is located at a first position 3. In act S30, a stationary field map 24 including information about a magnetic field distribution in the homogeneity volume 22 is provided, which is independent of the position of the movable patient support 2 and includes magnetic field components generated by stationary shim coils, as described above. In act S40, a position dependent field map 25 including information about a magnetic field distribution in the homogeneity volume 22 mainly influenced by a position of the movable patient support 2 is determined using the stationary field map 24 and the first resulting field map 23. In act S50, a second resulting field map 26 in the homogeneity volume 22 is determined when the movable patient support 2 is located at a second position 4 different from the first position 3, using the stationary field map 24 and the position dependent field map 25. The method ends in act S90.

The stationary contributions of the basic magnetic field may slightly change due to external influences, e.g., installation of another large device in the immediate neighborhood.

If averaging is carried out over many measurements B(x,y,z,SHIM,TP), then the influences of non-stationary magnetic fields are averaged, leaving a measure for the actual scanner inhomogeneity. This may be carried out continuously and thus possible changes in the scanner inhomogeneity may be detected. With self-learning algorithms, small changes may, if necessary, be directly implemented as corrections. In the case of large changes, a new determination of the basic magnetic field may be triggered.

Figure 5:
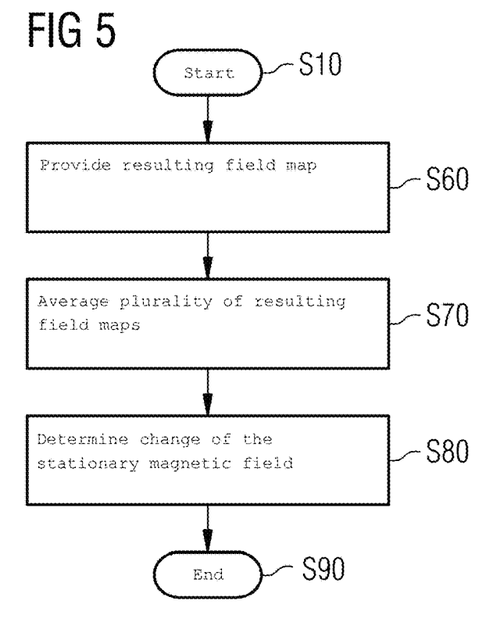
FIG. 5 schematically illustrates a flow chart with acts for performing a method for determining a change of a stationary magnetic field in a MR system with a movable patient support, according to certain embodiments.

FIG. 5 schematically illustrates a flow chart with acts for performing a method for determining a change of a stationary magnetic field 24 in a MR system 1 with a movable patient support 2.

The method starts in act S10. In act S60, a resulting field map 23 is provided for each of a plurality of different positions of the movable patient support 2, wherein the resulting field map 23 is based on a stationary magnetic field 24 substantially not influenced by position of the movable patient support 2 and a position dependent magnetic field 25 mainly influenced by each position of the movable patient support 2. In act S70, the plurality of resulting field maps 23 is averaged, e.g., an average is calculated between a plurality of resulting magnetic field values for each voxel. In act S80, a change of the stationary magnetic field 24 of the MR system 1 is determined based on the average of the plurality of resulting field maps 23. The method ends in act S90.

From the above, certain conclusions may be drawn:

The first resulting field map may be an absolute field map of the resulting magnetic field in the homogeneity volume as used for a MR measurement in the examination volume of the MR system. It may be measured by a 3-echo-method as known in the art. By providing an absolute field map as described above, a resulting magnetic field in the homogeneity volume and corresponding shim settings may be determined more reliably and more precisely.

Determining a position dependent field map may include calculating a difference between the first resulting field map and the stationary field map. Calculating a difference between the first resulting field map and the stationary field map provides efficient determination of position dependent magnetic field components in the homogeneity volume of the MR system.

The second resulting field map may be determined based on a displacement between the first and the second position of the movable patient support. In some embodiments the displacement takes place substantially in the z-direction of the MR system, in other embodiments, (e.g., in open C-shaped MR systems), the displacement may take place two dimensions, wherein the method may be applied to any displacement. By using the displacement between the first and the second position of the movable patient support, the information about position dependent magnetic field components corresponding to the patient support and the examination subject on the patient support used to more reliably and efficiently determine a magnetic field map and corresponding shim settings based on displacement of the patient support.

The second resulting field map may be determined using the position dependent field map, wherein the position of the position dependent field map is shifted relative to the stationary field map by the displacement of the movable patient support. Shifting the position of the position dependent field map according to the displacement of the movable patient support, allows to more reliably and efficiently determine a magnetic field map and corresponding shim settings based on displacement of the patient support.

The second resulting field map may be determined according to the relation:

$$B(x,y,z,\text{SHIM},TP2)=B_{DCS}(x,y,z,\text{SHIM}^{stat})+B_{table}(x,y,z-z_{TP1}+z_{TP2},\text{SHIM}^{move},TP1),$$

B(x,y,z,SHIM,TP2) is the second resulting field map; $B_{DCS}$(x,y,z,SHIM) is the stationary field map; $B_{table}$(x,y,z-$z_{TP1}$+$z_{TP2}$,SHIM$^{move}$,TP1) is the position dependent field map (measured at TP1) shifted by the displacement d=$z_{TP2}$-$z_{TP1}$; $z_{TP2}$ corresponds to the z-coordinate of the second position of the movable patient support; $z_{TP1}$ corresponds to the z-coordinate of the first position of the movable patient support; and wherein the overall shim condition SHIM= (SHIM$^{stat}$, SHIM$^{move}$) including a contribution SHIM$^{stat}$ by stationary shim coils, and a contribution SHIM$^{move}$ by movable Coilshims, which are moved together with the patient support. The relation described above enables a fast and efficient calculation of a magnetic field map and corresponding shim settings based on displacement of the patient support.

The position dependent field map may be substantially only influenced by the position of the movable patient support and components such as Coilshims, which are moved together with the patient support, relative to the stationary elements of the MR system. Therein, stationary magnetic field components based on stationary, non-movable elements in the MR-system, do not substantially influence the position dependent field map, and other magnetic field components which are based on elements movable with the patient support, such as Coilshims, the patient support itself and the patient mainly influence the position dependent field map. By considering mainly only magnetic field components dependent on position of the patient support, determination of a magnetic field map and corresponding shim settings based on displacement of the patient support may be performed more reliably and efficiently.

A second resulting field map may be only determined using the stationary field map and the position dependent field map, when the displacement is smaller than a movement threshold determined based on a following examination volume. In another embodiment, the second resulting field map may only be determined, if the adjustment volume for the following examining volume is within the intersection volume of the stationary field map and the position dependent field map. In this case, the threshold may be determined based on the relation of the adjustment volume to the intersection volume.

Using such a threshold provides more reliability and preciseness for the method, as positions of the patient support are excluded, where the patient support is moved as far to a position, where not enough information is available in the homogeneity volume to precisely determine a magnetic field map and corresponding shim settings.

The second resulting field map may be measured using MR signals from the homogeneity volume when the displacement is larger than a movement threshold determined based on the following examination volume. In particular, in order to enable the calculation of the second resulting field map, the threshold is chosen as large as possible.

For the so-called MDS adjustments, an isocentrically measured volume, which extends only a few centimeters in z-direction, is measured. According to the above-described method using absolute field maps, a plurality of N magnetic fields corresponding to different table positions $B_{table}$(TP1, SHIM$^{move}$) to $B_{table}$(TPN,SHIM$^{move}$) may be determined successively while the table moves from one table position to the next table position, (e.g., while the table moves continuously).

The extensions and distances in z-direction of this plurality of measurements are selected in such a way that a seamless map of the lying inhomogeneities may be calculated from $B_{table}$(TP1,SHIM$^{move}$) to $B_{table}$(TPN,SHIM$^{move}$): $B_{table}$(TP1–TPN,SHIM$^{move}$). The map may correspond to the complete body of a patient, or partial regions of the body of the patient, which are of interest for MR imaging. Thus, with one MDS-Adjustment-Scan the field map B(x,y,z, SHIM,TP) may be determined for each table position, and a complete shim calculation is performed thereon.

Accordingly, a resulting field map may be provided for each of a plurality of different positions of the movable patient support, a stationary field map including information about a magnetic field distribution in a homogeneity volume of the MR system, which is independent of the positions of the movable patient support may be provided, an overall position dependent field map including information about a magnetic field distribution mainly influenced by each position of the movable patient support may be determined using the stationary field map and the plurality of resulting field maps, and an intermediate resulting field map may be determined while the movable patient support is located at an intermediate position between two positions of the movable patient support, using the stationary field map and the overall position dependent field map. Using a plurality of position dependent field maps for a plurality of different patient support, which furthermore may be merged to an overall position dependent field map, enables determining accurate shim settings for all possible patient support positions lying between the measured patient support positions.

The different positions of the movable patient support are adjacent to each other or overlapping each other, whereby only one reference scan may be sufficient for a plurality of measurements on an examining position, without the need of recurring reference scans to determine new shim settings when the patient support is moved to an arbitrary intermediate position.

The method is performed using substantially continuous movement of the movable patient support, enabling a smooth transition for an examination subject and a more efficient method for determining new shim settings by only one reference scan.

Summarizing, a method for determining a field map and corresponding shim settings in a MR system including a movable patient support is provided, wherein an absolute B0 field map is used and magnetic field inhomogeneities are first separated into stationary magnetic field components and table position dependent magnetic field components, in order to then add these components again to determine a magnetic field map based on a new desired table position. Effectively, a significantly larger value for the table movement threshold may be used resulting in a saving of adjustment time and thus gives the customer more time for imaging, which may be used to more precisely and effectively determine a magnetic field map and corresponding shim settings, perform additional diagnostic measurements, or achieve shorter examination times.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for determining a field map in a magnetic resonance (MR) system comprising a movable patient support, the method comprising:
    providing a first resulting field map having position dependent information about a magnetic field distribution in a homogeneity volume comprising an examination volume of the MR system when the movable patient support is located at a first position;
    providing a stationary field map having information about a magnetic field distribution in the homogeneity volume, which is independent of the position of the movable patient support;
    determining a position dependent field map having information about a magnetic field distribution in the homogeneity volume influenced by a position of the movable patient support using the stationary field map and the first resulting field map; and
    determining a second resulting field map in the homogeneity volume when the movable patient support is located at a second position different from the first position, using the stationary field map and the position dependent field map.

2. The method of claim 1, wherein the first resulting field map is an absolute field map of a resulting magnetic field in the homogeneity volume as used for a MR measurement in the examination volume of the MR system.

3. The method of claim 2, wherein the second resulting field map is determined based on a displacement between the first and the second position of the movable patient support.

4. The method of claim 3, wherein the second resulting field map is determined using the position dependent field map, and
  wherein the position of the position dependent field map is shifted relative to the stationary field map by the displacement of the movable patient support.

5. The method of claim 1, wherein the determining of the position dependent field map comprises calculating a difference between the first resulting field map and the stationary field map.

6. The method of claim 1, wherein the second resulting field map is determined based on a displacement between the first and the second position of the movable patient support.

7. The method of claim 6, wherein the second resulting field map is determined using the position dependent field map, and
  wherein the position of the position dependent field map is shifted relative to the stationary field map by the displacement of the movable patient support.

8. The method of claim 7, wherein the second resulting field map is determined according to the relation:

$$B(x, y, z, SHIM, TP2) = B_{DCS}(x, y, z, SHIM^{stat}) + B_{table}(x, y, z - z_{TP1} + z_{TP2}, SHIM^{move}, TP1),$$

wherein:
  $B(x,y,z,SHIM,TP2)$ is the second resulting field map,
  $B_{DCS}(x,y,z,SHIM^{stat})$ is the stationary field map,
  $B_{table}(x,y,z-z_{TP1}+z_{TP2},SHIM^{move},TP1)$ is the position dependent field map shifted by the displacement $d=z_{TP2}-z_{TP1}$,
  $z_{TP2}$ corresponds to the z-coordinate of the second position of the movable patient support, and
  $z_{TP1}$ corresponds to the z-coordinate of the first position of the movable patient support, and
  wherein an overall shim condition $SHIM=(SHIM^{stat}, SHIM^{move})$ comprises a contribution $SHIM^{stat}$ by stationary shim coils, and a contribution $SHIM^{move}$ by movable Coilshims, which are moved together with the patient support.

9. The method of claim 8, wherein the second resulting field map is only determined using the stationary field map and the position dependent field map, when the displacement is smaller than a movement threshold determined based on a following examination volume.

10. The method of claim 9, wherein the second resulting field map is measured using MR signals from the homogeneity volume when the displacement is larger than the movement threshold determined based on the following examination volume.

11. The method of claim 7, wherein the second resulting field map is only determined using the stationary field map and the position dependent field map, when the displacement is smaller than a movement threshold determined based on a following examination volume.

12. The method of claim 11, wherein the second resulting field map is measured using MR signals from the homogeneity volume when the displacement is larger than the movement threshold determined based on the following examination volume.

13. The method of claim 1, wherein the position dependent field map is only influenced by the position of the movable patient support and shim coils moved together with the patient support relative to stationary elements of the MR system.

14. The method of claim 1, wherein a resulting field map is provided for each position of a plurality of different positions of the movable patient support, and
  wherein a stationary field map comprising information about a magnetic field distribution in a homogeneity volume of the MR system, which is independent of the positions of the movable patient support, is provided,
  wherein an overall position dependent field map comprising information about a magnetic field distribution influenced by each position of the movable patient support is determined using the stationary field map and the plurality of resulting field maps, and
  wherein an intermediate resulting field map is determined while the movable patient support is located at an intermediate position between two positions of the movable patient support, using the stationary field map and the overall position dependent field map.

15. The method of claim 14, wherein the different positions of the movable patient support are adjacent to each other or overlapping each other.

16. The method of claim 15, wherein the method is performed using continuous movement of the movable patient support.

17. The method of claim 14, wherein the method is performed using continuous movement of the movable patient support.

18. A method for determining a change of a stationary magnetic field in a magnetic resonance (MR) system with a movable patient support, the method comprising:
  providing a resulting field map for each of a plurality of different positions of the movable patient support, wherein the resulting field map is based on a stationary magnetic field not influenced by position of the movable patient support and a position dependent magnetic field influenced by each position of the movable patient support;
  averaging the plurality of resulting field maps; and
  determining a change of the stationary magnetic field of the MR system based on the average of the plurality of resulting field maps.

19. A magnetic resonance (MR) system with a movable patient support for determining a magnetic field map, the MR system comprising:
  a memory configured to store program code; and
  a MR controller coupled with the memory and configured to execute the program code, wherein execution of the program code by the MR controller is configured to cause the MR system to:
    provide a first resulting field map having position dependent information about a magnetic field distribution in a homogeneity volume comprising an examination volume of the MR system when the movable patient support is located at a first position;
    provide a stationary field map having information about a magnetic field distribution in the homogeneity volume, which is independent of the position of the movable patient support;
    determine a position dependent field map having information about a magnetic field distribution in the homogeneity volume influenced by a position of the movable patient support using the stationary field map and the first resulting field map; and
    determine a second resulting field map in the homogeneity volume when the movable patient support is located at a second position different from the first position, using the stationary field map and the position dependent field map.

\* \* \* \* \*